US012036230B2

United States Patent
Michael et al.

(10) Patent No.: US 12,036,230 B2
(45) Date of Patent: Jul. 16, 2024

(54) PTEN INHIBITORS FOR TREATMENT AND PREVENTION OF BONE MARROW LOSS

(71) Applicant: NISIBIS, LLC-S, Hammond, IN (US)

(72) Inventors: Ronald Michael, Hammond, IN (US); Fredrick N. Michael, Madison, AL (US)

(73) Assignee: NISIBIS, LLC-S, Hammond, IN (US)

( * ) Notice: Subject to any disclaimer, the term of this patent is extended or adjusted under 35 U.S.C. 154(b) by 0 days.

(21) Appl. No.: 18/174,989

(22) Filed: Feb. 27, 2023

(65) Prior Publication Data
US 2023/0218653 A1 Jul. 13, 2023

Related U.S. Application Data

(63) Continuation of application No. PCT/US2021/048012, filed on Aug. 27, 2021.

(60) Provisional application No. 63/071,825, filed on Aug. 28, 2020.

(51) Int. Cl.
| | |
|---|---|
| *A61K 31/7048* | (2006.01) |
| *A61K 31/404* | (2006.01) |
| *A61K 31/409* | (2006.01) |
| *A61K 31/655* | (2006.01) |
| *A61K 31/661* | (2006.01) |
| *A61K 31/7004* | (2006.01) |
| *A61K 31/702* | (2006.01) |
| *A61K 31/714* | (2006.01) |
| *A61K 45/06* | (2006.01) |

(52) U.S. Cl.
CPC ........ *A61K 31/7048* (2013.01); *A61K 31/404* (2013.01); *A61K 31/409* (2013.01); *A61K 31/655* (2013.01); *A61K 31/661* (2013.01); *A61K 31/7004* (2013.01); *A61K 31/702* (2013.01); *A61K 31/714* (2013.01); *A61K 45/06* (2013.01)

(58) Field of Classification Search
None
See application file for complete search history.

(56) References Cited

U.S. PATENT DOCUMENTS

| | | |
|---|---|---|
| 2004/0220167 A1 | 11/2004 | Samiy |
| 2007/0203098 A1 | 8/2007 | Garlich et al. |
| 2010/0113386 A1 | 5/2010 | Williams |
| 2011/0172179 A1* | 7/2011 | Prasad ................... A61P 39/06 514/354 |
| 2017/0319645 A1 | 11/2017 | Barnea |
| 2019/0224247 A1 | 7/2019 | Mori et al. |

FOREIGN PATENT DOCUMENTS

WO WO-2012027494 A1 3/2012

OTHER PUBLICATIONS

"Prevention" in Glossary of medical education terms: Parts 1-7. Wojtczak, A., Ed. Medical Teacher. vol. 24, Nos. 2-6 and vol. 25, No. 1&2. 2002. (Year: 2002).*
Morczek, A., & Schmidt, W. (1966). Effect of vitamin B 12 and folic acid on the radiation syndrome of total body irradiated rats. Radiobiologia, radiotherapia, 7(4), 487-494. (Year: 1966).*
Pany, J. (1957). Effects of levulose combined with vitamin B complex in radiation injuries. Wiener Zeitschrift fur innere Medizin und ihre Grenzgebiete, 38(6), 237-240. (Year: 1957).*
Berge, S.M., et al., "Pharmaceutical salts," J Pharm Sci 66(1):1-19, Elsevier, Netherlands (Jan. 1977).
Burdelya, L.G., et al., "An agonist of toll-like receptor 5 has radioprotective activity in mouse and primate models," Science 320(5873):226-230, American Association for the Advancement of Science, United States (Apr. 2008).
International Search Report and Written Opinion for International Application No. PCT/US2021/048012, Commissioner for Patents, United States, mailed on Feb. 8, 2022, 12 pages.

* cited by examiner

*Primary Examiner* — Dale R Miller
(74) *Attorney, Agent, or Firm* — Sterne, Kessler, Goldstein & Fox P.L.L.C.

(57) ABSTRACT

The present disclosure relates to pharmaceutical compositions comprising PTEN inhibitors and methods of treating or preventing bone marrow loss in subjects in subjects in need thereof. The compositions and methods of this disclosure are useful in treating or preventing bone marrow loss associated with exposure to nuclear radiation or chemotherapeutic treatment.

13 Claims, No Drawings

_US 12,036,230 B2_

PTEN INHIBITORS FOR TREATMENT AND PREVENTION OF BONE MARROW LOSS

CROSS REFERENCE TO RELATED APPLICATIONS

The present application is a continuation of PCT Application No. PCT/US2021/048012, filed on Aug. 27, 2021, which claims the benefit of priority to U.S. Provisional Application No. 63/071,825, filed on Aug. 28, 2020, the contents of both of which are hereby incorporated by reference in their entireties.

FIELD OF THE INVENTION

The present disclosure relates to pharmaceutical compositions of PTEN inhibitors and methods of administering such pharmaceutical compositions to treat or prevent bone marrow loss, such as bone marrow loss associated with exposure to nuclear radiation or a chemotherapeutic treatment for cancer.

BACKGROUND

Following a nuclear accident or attack, the majority of deaths in those not killed from the blast are a result of bone marrow failure. Nuclear radiation affects rapidly dividing cells more than those that do not divide as rapidly, and bone marrow cells are among the most vulnerable of these rapidly dividing cells. Apoptosis, or programmed cell death, rids the body of damaged cells, but many of these cells could repair themselves if not for apoptotic pathways. Gudkov et al (Science 320, 226 (2008)) demonstrated improved survival in animals subjected to a lethal dose of radiation by treating them with a purified *Salmonella* flagellin protein. The flagellin protein stimulates cell surface Toll Like Receptor 5, leading ultimately to activation of NfκB, which activates survival pathways.

Bone marrow loss is also observed in patients receiving chemotherapeutic treatment for proliferative disease. When oncologists treat patients with chemotherapy or radiation therapy, the dose is limited by how much damage is done to the bone marrow. An oncologist must stop treatment, prescribe medications to improve bone marrow health (e.g., EPOGEN®, NEUPOGEN®, NEULASTA), and then resume treatment once the bone marrow has recovered. However, a temporary or prolonged cessation of chemotherapeutic treatment may limit its efficacy and lead to poor patient outcomes.

PTEN (phosphatase and tensin homolog deleted on chromosome 10) controls intracellular signaling for cell survival and proliferation by inhibiting the PI3K/Akt pathway. As a result of PTEN mediated PI3K/Akt pathway inhibition, downstream activation of immunity and cell survival genes by NFκB is downregulated. PTEN mediated downregulation of the immunity and cell survival processes leads to apoptosis in subjects exposed to nuclear radiation and subjects undergoing certain chemotherapeutic treatment for proliferative disease. As a result, these subjects experience a loss of bone marrow.

Therefore, there is a need for pharmaceutical compositions of PTEN inhibitors for the treatment and prevention of bone marrow loss associated with exposure to nuclear radiation or chemotherapeutic treatment.

BRIEF SUMMARY OF THE INVENTION

The present disclosure features useful compositions and methods for the treatment and prevention of bone marrow loss associated with exposure to nuclear radiation or chemotherapeutic treatment.

In some aspects, the present disclosure provides a method of treating a disease, disorder, syndrome, or condition amenable to treatment by a PTEN inhibitor in a subject in need thereof, comprising administering to the subject an effective amount of a PTEN inhibitor selected from the group consisting of: verteporfin or a pharmaceutically acceptable salt thereof; candicidin or a pharmaceutically acceptable salt thereof; cyanocobalamin or a pharmaceutically acceptable salt thereof; 1-palmitoyl-2-oleoyl-sn-glycero-3-(phospho-rac-(1-glycerol)) or a pharmaceutically acceptable salt thereof; fondaparinux or a pharmaceutically acceptable salt thereof; trypan blue free acid or a pharmaceutically acceptable salt thereof; indocyanine green acid form or a pharmaceutically acceptable salt thereof; DL-dimyristoylphosphatidylglycerol or a pharmaceutically acceptable salt thereof; and tannic acid or a pharmaceutically acceptable salt thereof.

In some aspects, the disease, disorder, syndrome, or condition is selected from the group consisting of: Acute Radiation Syndrome; Alzheimer's disease; aplastic anemia; a pathology in bone formation; bone marrow failure; cerebrovascular accident; diabetes mellitus type 2; obesity; hair loss; Huntington's disease; a myelodysplastic syndrome; myocardial ischemia; myocardial infarction; Parkinson's disease; renal failure; rheumatoid arthritis; sepsis; schizophrenia; spinal cord injury; traumatic brain injury; a pathology in wound healing; amyotrophic lateral sclerosis; and Duchenne muscular dystrophy. In some aspects, the disease, disorder, syndrome, or condition is Acute Radiation Syndrome. In some aspects, the disease, disorder, syndrome, or condition is Alzheimer's disease. In some aspects, the disease, disorder, syndrome, or condition is aplastic anemia. In some aspects, the disease, disorder, syndrome, or condition is a pathology in bone formation. In some aspects, the disease, disorder, syndrome, or condition is bone marrow failure. In some aspects, the disease, disorder, syndrome, or condition is cerebrovascular accident. In some aspects, the disease, disorder, syndrome, or condition is diabetes mellitus type 2. In some aspects, the disease, disorder, syndrome, or condition is obesity. In some aspects, the disease, disorder, syndrome, or condition is hair loss. In some aspects, the disease, disorder, syndrome, or condition is Huntington's disease. In some aspects, the disease, disorder, syndrome, or condition is a myelodysplastic syndrome. In some aspects, the disease, disorder, syndrome, or condition is myocardial ischemia. In some aspects, the disease, disorder, syndrome, or condition is myocardial infarction. In some aspects, the disease, disorder, syndrome, or condition is Parkinson's disease. In some aspects, the disease, disorder, syndrome, or condition is renal failure. In some aspects, the disease, disorder, syndrome, or condition is rheumatoid arthritis. In some aspects, the disease, disorder, syndrome, or condition is sepsis. In some aspects, the disease, disorder, syndrome, or condition is schizophrenia. In some aspects, the disease, disorder, syndrome, or condition is spinal cord injury. In some aspects, the disease, disorder, syndrome, or condition is traumatic brain injury. In some aspects, the disease, disorder, syndrome, or condition is a pathology in wound healing. In some aspects, the disease, disorder, syndrome, or condition is amyotrophic lateral sclerosis. In some aspects, the disease, disorder, syndrome, or condition is Duchenne muscular dystrophy.

In some aspects, the present disclosure provides a method of regenerating bone marrow in a subject in need thereof, comprising administering to the subject an effective amount of a PTEN inhibitor selected from the group consisting of: verteporfin or a pharmaceutically acceptable salt thereof; candicidin or a pharmaceutically acceptable salt thereof; cyanocobalamin or a pharmaceutically acceptable salt thereof; 1-palmitoyl-2-oleoyl-sn-glycero-3-(phospho-rac-(1-glycerol)) or a pharmaceutically acceptable salt thereof; fondaparinux or a pharmaceutically acceptable salt thereof; trypan blue free acid or a pharmaceutically acceptable salt thereof; indocyanine green acid form or a pharmaceutically acceptable salt thereof; DL-dimyristoylphosphatidylglycerol or a pharmaceutically acceptable salt thereof; and tannic acid or a pharmaceutically acceptable salt thereof.

In some aspects, the subject has been diagnosed with bone marrow loss. In some aspects, the subject has been diagnosed with neutropenia. In some aspects, the subject has been diagnosed with aplastic anemia. In some aspects, the subject has been diagnosed with myelodysplastic syndrome.

In some aspects, the PTEN inhibitor is administered in an amount effective in restoring bone marrow to substantially the same amount of bone marrow present in the subject prior to bone marrow loss.

In some aspects, the subject experiences bone marrow loss after treatment with a chemotherapeutic agent. In some aspects, the chemotherapeutic agent has been administered to the subject as a treatment for a cancer or a tumor.

In some aspects, the PTEN inhibitor is administered after treatment with the chemotherapeutic agent has been ceased.

In some aspects, the subject experiences bone marrow loss as a result of exposure to nuclear radiation. In some aspects, the subject has been diagnosed with Acute Radiation Syndrome.

In some aspects, the present disclosure provides a method of reducing at least one side effect associated with a chemotherapeutic agent in a subject in need thereof comprising administering to the subject an effective amount of a PTEN inhibitor selected from the group consisting of: verteporfin or a pharmaceutically acceptable salt thereof; candicidin or a pharmaceutically acceptable salt thereof; cyanocobalamin or a pharmaceutically acceptable salt thereof; 1-palmitoyl-2-oleoyl-sn-glycero-3-(phospho-rac-(1-glycerol)) or a pharmaceutically acceptable salt thereof; fondaparinux or a pharmaceutically acceptable salt thereof; trypan blue free acid or a pharmaceutically acceptable salt thereof; indocyanine green acid form or a pharmaceutically acceptable salt thereof; DL-dimyristoylphosphatidylglycerol or a pharmaceutically acceptable salt thereof; and tannic acid or a pharmaceutically acceptable salt thereof.

In some aspects, the at least one side effect is increased apoptosis.

In some aspects, the at least one side effect is bone marrow loss. In some aspects, the PTEN inhibitor is administered after bone marrow loss has been determined.

In some aspects, the at least one side effect is damage to the gastrointestinal epithelium.

In some aspects, the at least one side effect is an increased risk of infection.

In some aspects, the PTEN inhibitor is administered prior to administration of the chemotherapeutic agent. In some aspects, the PTEN inhibitor is administered about 1 hour to about 2 weeks prior to administration of the chemotherapeutic agent. In some aspects, the PTEN inhibitor is administered about 2 weeks prior to administration of the chemotherapeutic agent. In some aspects, the PTEN inhibitor is administered about 1 week prior to administration of the chemotherapeutic agent. In some aspects, the PTEN inhibitor is administered about 6 days prior to administration of the chemotherapeutic agent. In some aspects, the PTEN inhibitor is administered about 5 days prior to administration of the chemotherapeutic agent. In some aspects, the PTEN inhibitor is administered about 4 days prior to administration of the chemotherapeutic agent. In some aspects, the PTEN inhibitor is administered about 3 days prior to administration of the chemotherapeutic agent. In some aspects, the PTEN inhibitor is administered about 2 days prior to administration of the chemotherapeutic agent. In some aspects, the PTEN inhibitor is administered about 1 day prior to administration of the chemotherapeutic agent. In some aspects, the PTEN inhibitor is administered about 12 hours prior to administration of the chemotherapeutic agent. In some aspects, the PTEN inhibitor is administered about 8 hours prior to administration of the chemotherapeutic agent. In some aspects, the PTEN inhibitor is administered about 6 hours prior to administration of the chemotherapeutic agent. In some aspects, the PTEN inhibitor is administered about 4 hours prior to administration of the chemotherapeutic agent. In some aspects, the PTEN inhibitor is administered about 3 hours prior to administration of the chemotherapeutic agent. In some aspects, the PTEN inhibitor is administered about 2 hours prior to administration of the chemotherapeutic agent. In some aspects, the PTEN inhibitor is administered about 1 hour prior to administration of the chemotherapeutic agent.

In some aspects, the PTEN inhibitor is coadministered with the chemotherapeutic agent.

In some aspects, the PTEN inhibitor is administered after administration of the chemotherapeutic agent. In some aspects, the PTEN inhibitor is administered about 1 hour to about 2 weeks after administration of the chemotherapeutic agent. In some aspects, the PTEN inhibitor is administered about 2 weeks after administration of the chemotherapeutic agent. In some aspects, the PTEN inhibitor is administered about 1 week after administration of the chemotherapeutic agent. In some aspects, the PTEN inhibitor is administered about 6 days after administration of the chemotherapeutic agent. In some aspects, the PTEN inhibitor is administered about 5 days after administration of the chemotherapeutic agent. In some aspects, the PTEN inhibitor is administered about 4 days after administration of the chemotherapeutic agent. In some aspects, the PTEN inhibitor is administered about 3 days after administration of the chemotherapeutic agent. In some aspects, the PTEN inhibitor is administered about 2 days after administration of the chemotherapeutic agent. In some aspects, the PTEN inhibitor is administered about 1 day after administration of the chemotherapeutic agent. In some aspects, the PTEN inhibitor is administered about 12 hours after administration of the chemotherapeutic agent. In some aspects, the PTEN inhibitor is administered about 8 hours after administration of the chemotherapeutic agent. In some aspects, the PTEN inhibitor is administered about 6 hours after administration of the chemotherapeutic agent. In some aspects, the PTEN inhibitor is administered about 4 hours after administration of the chemotherapeutic agent. In some aspects, the PTEN inhibitor is administered about 3 hours after administration of the chemotherapeutic agent. In some aspects, the PTEN inhibitor is administered about 2 hours after administration of the chemotherapeutic agent. In some aspects, the PTEN inhibitor is administered about 1 hour after administration of the chemotherapeutic agent.

In some aspects, the PTEN inhibitor is administered in an amount effective to increase the tolerated duration of treatment with the chemotherapeutic agent or the tolerated amount of treatment with the chemotherapeutic agent.

In some aspects, the chemotherapeutic agent is administered as a treatment for a cancer is selected from the group consisting of: skin cancer, malignant peripheral nerve sheath cancer, leukemia, lymphoma, histiocytic neoplasm, lung cancer, breast cancer, ovarian cancer, renal cancer, colorectal cancer, thyroid cancer, cholangiocarcinoma, urothelial cancer, uterine neoplasm, gastric cancer, sarcoma, bladder cancer, head and neck cancer, endometrial cancer, esophageal cancer, adenoid cystic carcinoma, gallbladder cancer, prostate cancer, oral cancer, cervical cancer, pancreatic cancer, melanoma, hepatocellular cancer, biliary tract cancer, and serous carcinoma of the peritoneum.

In some aspects, the present disclosure provides a method of treating exposure to nuclear radiation in a subject in need thereof, the method comprising administering to the subject an effective amount of a PTEN inhibitor selected from the group consisting of: verteporfin or a pharmaceutically acceptable salt thereof; candicidin or a pharmaceutically acceptable salt thereof; cyanocobalamin or a pharmaceutically acceptable salt thereof; 1-palmitoyl-2-oleoyl-sn-glycero-3-(phospho-rac-(1-glycerol)) or a pharmaceutically acceptable salt thereof; fondaparinux or a pharmaceutically acceptable salt thereof; trypan blue free acid or a pharmaceutically acceptable salt thereof; indocyanine green acid form or a pharmaceutically acceptable salt thereof; DL-dimyristoylphosphatidylglycerol or a pharmaceutically acceptable salt thereof; and tannic acid or a pharmaceutically acceptable salt thereof.

In some aspects, the PTEN inhibitor is administered in an amount effective to reduce apoptosis in the subject caused by exposure to nuclear radiation. In some aspects, the PTEN inhibitor is administered in an amount effective to reduce bone marrow loss in the subject caused by exposure to nuclear radiation. In some aspects, the PTEN inhibitor is administered in an amount effective to reduce damage to the gastrointestinal epithelium in the subject caused by exposure to nuclear radiation. In some aspects, the PTEN inhibitor is administered in an amount effective to reduce an increased risk of infection in the subject caused by exposure to nuclear radiation.

In some aspects, the PTEN inhibitor is administered about 1 hour to about 2 weeks after exposure to nuclear radiation. In some aspects, the PTEN inhibitor is administered about 2 weeks after exposure to nuclear radiation. In some aspects, the PTEN inhibitor is administered about 1 week after exposure to nuclear radiation. In some aspects, the PTEN inhibitor is administered about 6 days after exposure to nuclear radiation. In some aspects, the PTEN inhibitor is administered about 5 days after exposure to nuclear radiation. In some aspects, the PTEN inhibitor is administered about 4 days after exposure to nuclear radiation. In some aspects, the PTEN inhibitor is administered about 3 days after exposure to nuclear radiation. In some aspects, the PTEN inhibitor is administered about 2 days after exposure to nuclear radiation. In some aspects, the PTEN inhibitor is administered about 1 day after exposure to nuclear radiation. In some aspects, the PTEN inhibitor is administered about 12 hours after exposure to nuclear radiation. In some aspects, the PTEN inhibitor is administered about 8 hours after exposure to nuclear radiation. In some aspects, the PTEN inhibitor is administered about 6 hours after exposure to nuclear radiation. In some aspects, the PTEN inhibitor is administered about 4 hours after exposure to nuclear radiation. In some aspects, the PTEN inhibitor is administered about 3 hours after exposure to nuclear radiation. In some aspects, the PTEN inhibitor is administered about 2 hours after exposure to nuclear radiation. In some aspects, the PTEN inhibitor is administered about 1 hour after exposure to nuclear radiation.

In some aspects, the subject has been diagnosed with Acute Radiation Syndrome.

In some aspects, the present disclosure provides a method of preventing Acute Radiation Syndrome in a subject in need thereof, the method comprising administering to the subject an effective amount of a PTEN inhibitor selected from the group consisting of: verteporfin or a pharmaceutically acceptable salt thereof; candicidin or a pharmaceutically acceptable salt thereof; cyanocobalamin or a pharmaceutically acceptable salt thereof; 1-palmitoyl-2-oleoyl-sn-glycero-3-(phospho-rac-(1-glycerol)) or a pharmaceutically acceptable salt thereof; fondaparinux or a pharmaceutically acceptable salt thereof; trypan blue free acid or a pharmaceutically acceptable salt thereof; indocyanine green acid form or a pharmaceutically acceptable salt thereof; DL-dimyristoylphosphatidylglycerol or a pharmaceutically acceptable salt thereof; and tannic acid or a pharmaceutically acceptable salt thereof; wherein the PTEN inhibitor is administered prior to or during exposure of the subject to nuclear radiation.

In some aspects, the PTEN inhibitor is administered prior to exposure to nuclear radiation. In some aspects, the PTEN inhibitor is administered about 1 hour to about 2 weeks prior to exposure to nuclear radiation. In some aspects, the PTEN inhibitor is administered about 2 weeks prior to exposure to nuclear radiation. In some aspects, the PTEN inhibitor is administered about 1 week prior to exposure to nuclear radiation. In some aspects, the PTEN inhibitor is administered about 6 days prior to exposure to nuclear radiation. In some aspects, the PTEN inhibitor is administered about 5 days prior to exposure to nuclear radiation. In some aspects, the PTEN inhibitor is administered about 4 days prior to exposure to nuclear radiation. In some aspects, the PTEN inhibitor is administered about 3 days prior to exposure to nuclear radiation. In some aspects, the PTEN inhibitor is administered about 2 days prior to exposure to nuclear radiation. In some aspects, the PTEN inhibitor is administered about 1 day prior to exposure to nuclear radiation. In some aspects, the PTEN inhibitor is administered about 12 hours prior to exposure to nuclear radiation. In some aspects, the PTEN inhibitor is administered about 8 hours prior to exposure to nuclear radiation. In some aspects, the PTEN inhibitor is administered about 6 hours prior to exposure to nuclear radiation. In some aspects, the PTEN inhibitor is administered about 4 hours prior to exposure to nuclear radiation. In some aspects, the PTEN inhibitor is administered about 3 hours prior to exposure to nuclear radiation. In some aspects, the PTEN inhibitor is administered about 2 hours prior to exposure to nuclear radiation. In some aspects, the PTEN inhibitor is administered about 1 hour prior to exposure to nuclear radiation.

In some aspects, the PTEN inhibitor is administered during exposure to nuclear radiation.

In some aspects, the PTEN inhibitor is verteporfin or a pharmaceutically acceptable salt thereof. In some aspects, the PTEN inhibitor is candicidin or a pharmaceutically acceptable salt thereof. In some aspects, the PTEN inhibitor is cyanocobalamin or a pharmaceutically acceptable salt thereof. In some aspects, the PTEN inhibitor is 1-palmitoyl-2-oleoyl-sn-glycero-3-(phospho-rac-(1-glycerol)) or a pharmaceutically acceptable salt thereof. In some aspects, the PTEN inhibitor is fondaparinux or a pharmaceutically acceptable salt thereof. In some aspects, the PTEN inhibitor is trypan blue free acid or a pharmaceutically acceptable salt thereof. In some aspects, the PTEN inhibitor is indocyanine green acid form or a pharmaceutically acceptable salt thereof. In some aspects, the PTEN inhibitor is DL-dimyristoylphosphatidylglycerol or a pharmaceutically acceptable salt thereof. In some aspects, the PTEN inhibitor is tannic acid or a pharmaceutically acceptable salt thereof.

In some aspects, a pharmaceutical composition comprises the PTEN inhibitor. In some aspects, the pharmaceutical composition further comprises a pharmaceutically acceptable carrier.

In some aspects, the pharmaceutical composition is a solid dosage form. In some aspects, the pharmaceutical composition is a tablet or capsule. In some aspects, the pharmaceutical composition is a tablet. In some aspects, the pharmaceutical composition is a capsule.

In some aspects, the pharmaceutical composition is for oral administration.

In some aspects, the pharmaceutical composition is administered parenterally. In some aspects, the pharmaceutical composition is administered intravenously. In some aspects, the pharmaceutical composition is administered intramuscularly. In some aspects, the pharmaceutical composition is administered subcutaneously.

In some aspects, the subject is a human.

In some aspects, administration of an amount of the PTEN inhibitor is as effective or more effective in activating NFκB in the subject as administration of an equimolar amount of a flagellin protein purified from Salmonella enterica.

Definitions

To facilitate understanding of the disclosure set forth herein, a number of terms are defined below.

Generally, the nomenclature used herein and the laboratory procedures in organic chemistry, medicinal chemistry, and pharmacology described herein are those well-known and commonly employed in the art. Unless defined otherwise, all technical and scientific terms (e.g., chemical names including informal, trivial, or semitrivial names) used herein generally have the same meaning as commonly understood by one of ordinary skill in the art to which this disclosure belongs.

In this specification and the appended claims, the singular forms "a," "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

As used herein, the terms "treat," "treated," and "treating" mean therapeutic treatment wherein the object is to slow down (lessen) an undesired physiological condition, disorder, or disease, or obtain beneficial or desired clinical results. Thus, those in need of treatment include those already diagnosed with or suspected of having the disorder. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment. The term "therapeutically effective amount" or "effective amount" is meant to include the amount of a compound that, when administered, is sufficient to prevent development of, or alleviate to some extent, one or more of the symptoms of a disorder, disease, or condition being treated. The term "therapeutically effective amount" or "effective amount" also refers to the amount of a compound that is sufficient to elicit the biological or medical response of a cell, tissue, system, animal, or human, which is being sought by a researcher, veterinarian, medical doctor, or clinician.

The terms "pharmaceutically acceptable carrier," "pharmaceutically acceptable excipient," "physiologically acceptable carrier," or "physiologically acceptable excipient" refer to a pharmaceutically-acceptable material, composition, or vehicle, such as a liquid or solid filler, diluent, excipient, solvent, or encapsulating material. In one aspect, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See Remington: The Science and Practice of Pharmacy, 21$^{st}$ Edition, Lippincott Williams & Wilkins: Philadelphia, PA, 2005; Handbook of Pharmaceutical Excipients, 5$^{th}$ Edition, Rowe et al., Eds., The Pharmaceutical Press and the American Pharmaceutical Association: 2005; and Handbook of Pharmaceutical Additives, 3$^{rd}$ Edition, Ash and Ash Eds., Gower Publishing Company: 2007; Pharmaceutical Preformulation and Formulation, Gibson Ed., CRC Press LLC: Boca Raton, FL, 2004 (incorporated herein by reference). Excipients can include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

The term "pharmaceutical composition," as used herein, represents a composition containing a compound described herein formulated with a pharmaceutically acceptable excipient, and can be manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); for intrathecal injection; for intracerebroventricular injections; for intraparenchymal injection; or in any other pharmaceutically acceptable formulation.

The term "pharmaceutically-acceptable salts" refers to the relatively non-toxic, inorganic and organic acid addition salts of a PTEN inhibitor described herein. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In certain aspects, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, e.g., Berge et al., supra).

The terms "about" or "approximately" means within a range of an acceptable error for a particular value as determined by one of ordinary skill in the art, which depends in part, on how the value is measured or determined. In certain aspects, the term "about" or "approximately" means within 1, 2, 3, or 4 standard deviations. In some aspects, the term "about" or "approximately" means a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

As used herein, the term "administration" refers to the administration of a composition (e.g., a compound or a preparation that includes a compound as described herein) to a subject or system. Administration to an animal subject (e.g., to a human) can be by any appropriate route, such as one described herein.

The terms "co-administration", "co-administering", or "co-administered" refer to administering a combination of therapeutic agents, such as, for example, a combination of a PTEN inhibitor described herein and another therapeutic agent. The combination can be administered as two separate entities, such as, for example, in separate capsules or tablets, or as a single combination entity, such as, for example, in the same capsule or tablet. One therapeutic agent (e.g., a PTEN inhibitor described herein) can be administered before, concomitantly, or subsequently to the administering of the other therapeutic agent (e.g., a chemotherapeutic agent) to the subject.

As used herein, the term "Acute Radiation Syndrome" or "ARS" refers to an acute illness caused by irradiation of the entire body or most of the body by a high dose of penetrating nuclear radiation in a short period of time. The major cause of this syndrome is depletion of immature parenchymal stem cells in specific tissues. Examples of people who suffered from ARS are the survivors of the Hiroshima and Nagasaki atomic bombs, the firefighters that first responded after the Chernobyl Nuclear Power Plant event in 1986, and some unintentional exposures to sterilization irradiators.

As used herein, the term "chemotherapeutic agent" refers to antineoplastic agents used to directly or indirectly inhibit proliferation of rapidly growing cells, typically in the context of malignancy. Certain chemotherapeutic agents are understood to effect a loss of bone marrow in a subject.

As used herein, the term "PTEN" refers to the protein designated phosphatase and tensin homolog, which is encoded by the PTEN gene in humans.

As used herein, the term "PTEN inhibitor" refers to a compound which effects a decrease in the rate of phosphatase activity of PTEN. Whereas many of the exemplary aspects disclosed herein describe PTEN activity and inhibition in the context of humans, those aspects are non-limiting, and inhibition of PTEN in non-human animals is also disclosed.

It is understood that wherever aspects are described herein with the language "comprising," otherwise analogous aspects described in terms of "consisting of" and/or "consisting essentially of" are also provided.

The details of one or more aspects are set forth in the description below. Other features, objects, and advantages will be apparent from the description and from the claims.

DETAILED DESCRIPTION OF THE INVENTION

In some aspects, the present disclosure provides a method of treating a disease, disorder, syndrome, or condition amenable to treatment by a PTEN inhibitor in a subject in need thereof, comprising administering to the subject an effective amount of a PTEN inhibitor selected from the group consisting of: verteporfin or a pharmaceutically acceptable salt thereof; candicidin or a pharmaceutically acceptable salt thereof; cyanocobalamin or a pharmaceutically acceptable salt thereof; 1-palmitoyl-2-oleoyl-sn-glycero-3-(phospho-rac-(1-glycerol)) or a pharmaceutically acceptable salt thereof; fondaparinux or a pharmaceutically acceptable salt thereof; trypan blue free acid or a pharmaceutically acceptable salt thereof; indocyanine green acid form or a pharmaceutically acceptable salt thereof; DL-dimyristoylphosphatidylglycerol or a pharmaceutically acceptable salt thereof; and tannic acid or a pharmaceutically acceptable salt thereof.

In some aspects, the disease, disorder, syndrome, or condition is selected from the group consisting of: Acute Radiation Syndrome; Alzheimer's disease; aplastic anemia; a pathology in bone formation; bone marrow failure; cerebrovascular accident; diabetes mellitus type 2; obesity; hair loss; Huntington's disease; a myelodysplastic syndrome; myocardial ischemia; myocardial infarction; Parkinson's disease; renal failure; rheumatoid arthritis; sepsis; schizophrenia; spinal cord injury; traumatic brain injury; a pathology in wound healing; amyotrophic lateral sclerosis; and Duchenne muscular dystrophy. In some aspects, the disease, disorder, syndrome, or condition is Acute Radiation Syndrome. In some aspects, the disease, disorder, syndrome, or condition is Alzheimer's disease. In some aspects, the disease, disorder, syndrome, or condition is aplastic anemia. In some aspects, the disease, disorder, syndrome, or condition is a pathology in bone formation. In some aspects, the disease, disorder, syndrome, or condition is bone marrow failure. In some aspects, the disease, disorder, syndrome, or condition is cerebrovascular accident. In some aspects, the disease, disorder, syndrome, or condition is diabetes mellitus type 2. In some aspects, the disease, disorder, syndrome, or condition is obesity. In some aspects, the disease, disorder, syndrome, or condition is hair loss. In some aspects, the disease, disorder, syndrome, or condition is Huntington's disease. In some aspects, the disease, disorder, syndrome, or condition is a myelodysplastic syndrome. In some aspects, the disease, disorder, syndrome, or condition is myocardial ischemia. In some aspects, the disease, disorder, syndrome, or condition is myocardial infarction. In some aspects, the disease, disorder, syndrome, or condition is Parkinson's disease. In some aspects, the disease, disorder, syndrome, or condition is renal failure. In some aspects, the disease, disorder, syndrome, or condition is rheumatoid arthritis. In some aspects, the disease, disorder, syndrome, or condition is sepsis. In some aspects, the disease, disorder, syndrome, or condition is schizophrenia. In some aspects, the disease, disorder, syndrome, or condition is spinal cord injury. In some aspects, the disease, disorder, syndrome, or condition is traumatic brain injury. In some aspects, the disease, disorder, syndrome, or condition is a pathology in wound healing. In some aspects, the disease, disorder, syndrome, or condition is amyotrophic lateral sclerosis. In some aspects, the disease, disorder, syndrome, or condition is Duchenne muscular dystrophy.

In some aspects, the present disclosure provides a method of regenerating bone marrow in a subject in need thereof, comprising administering to the subject an effective amount of a PTEN inhibitor. In some aspects, the present disclosure provides a method of regenerating bone marrow in a subject in need thereof, comprising administering to the subject an effective amount of a PTEN inhibitor selected from the group consisting of: 1-palmitoyl-2-oleoyl-sn-glycero-3-(phospho-rac-(1-glycerol)), candicidin, cobicistat, cyanocobalamin, diacetyl benzoyl lathyrol, DL-dimyristoylphosphatidylglycerol, everolimus, fondaparinux, indocyanine green acid form, levosimendan, oftasceine, tannic acid, trypan blue free acid, and verteporfin. In some aspects, the present disclosure provides a method of regenerating bone marrow in a subject in need thereof, comprising administering to the subject an effective amount of a PTEN inhibitor selected from the group consisting of: verteporfin or a pharmaceutically acceptable salt thereof; candicidin or a pharmaceutically acceptable salt thereof; cyanocobalamin or a pharmaceutically acceptable salt thereof; 1-palmitoyl-2-oleoyl-sn-glycero-3-(phospho-rac-(1-glycerol)) or a pharmaceutically acceptable salt thereof; fondaparinux or a pharmaceutically acceptable salt thereof; trypan blue free acid or a pharmaceutically acceptable salt thereof; indocyanine green acid form or a pharmaceutically acceptable salt thereof; DL-dimyristoylphosphatidylglycerol or a pharmaceutically acceptable salt thereof; and tannic acid or a pharmaceutically acceptable salt thereof.

In some aspects, the subject has been diagnosed with bone marrow loss. In some aspects, the subject has been diagnosed with neutropenia. In some aspects, the subject has been diagnosed with aplastic anemia. In some aspects, the subject has been diagnosed with myelodysplastic syndrome.

In some aspects, the PTEN inhibitor is administered in an amount effective in restoring bone marrow to substantially the same amount of bone marrow present in the subject prior to bone marrow loss.

In some aspects, the subject experiences bone marrow loss after treatment with a chemotherapeutic agent. In some aspects, the chemotherapeutic agent has been administered to the subject as a treatment for a cancer or a tumor.

In some aspects, the PTEN inhibitor is administered after treatment with the chemotherapeutic agent has been ceased.

In some aspects, the subject experiences bone marrow loss as a result of exposure to nuclear radiation. In some aspects, the subject has been diagnosed with Acute Radiation Syndrome.

In some aspects, the present disclosure provides a method of reducing at least one side effect associated with a chemotherapeutic agent in a subject in need thereof comprising administering to the subject an effective amount of a PTEN inhibitor. In some aspects, the present disclosure provides a method of reducing at least one side effect associated with a chemotherapeutic agent in a subject in need thereof comprising administering to the subject an effective amount of a PTEN inhibitor selected from the group consisting of: 1-palmitoyl-2-oleoyl-sn-glycero-3-(phospho-rac-(1-glycerol)), candicidin, cobicistat, cyanocobalamin, diacetyl benzoyl lathyrol, DL-dimyristoylphosphatidylglycerol, everolimus, fondaparinux, indocyanine green acid form, levosimendan, oftasceine, tannic acid, trypan blue free acid, and verteporfin. In some aspects, the present disclosure provides a method of reducing at least one side effect associated with a chemotherapeutic agent in a subject in need thereof comprising administering to the subject an effective amount of a PTEN inhibitor selected from the group consisting of: verteporfin or a pharmaceutically acceptable salt thereof; candicidin or a pharmaceutically acceptable salt thereof; cyanocobalamin or a pharmaceutically acceptable salt thereof; 1-palmitoyl-2-oleoyl-sn-glycero-3-(phospho-rac-(1-glycerol)) or a pharmaceutically acceptable salt thereof; fondaparinux or a pharmaceutically acceptable salt thereof; trypan blue free acid or a pharmaceutically acceptable salt thereof; indocyanine green acid form or a pharmaceutically acceptable salt thereof; DL-dimyristoylphosphatidylglycerol or a pharmaceutically acceptable salt thereof; and tannic acid or a pharmaceutically acceptable salt thereof.

In some aspects, the at least one side effect is increased apoptosis.

In some aspects, the at least one side effect is bone marrow loss. In some aspects, the PTEN inhibitor is administered after bone marrow loss has been determined.

In some aspects, the at least one side effect is damage to the gastrointestinal epithelium.

In some aspects, the at least one side effect is an increased risk of infection.

In some aspects, the PTEN inhibitor is administered prior to administration of the chemotherapeutic agent. In some aspects, the PTEN inhibitor is administered about 1 hour to about 2 weeks prior to administration of the chemotherapeutic agent. In some aspects, the PTEN inhibitor is administered about 1 hour to about 1 week prior to administration of the chemotherapeutic agent. In some aspects, the PTEN inhibitor is administered about 1 hour to about 6 days prior to administration of the chemotherapeutic agent. In some aspects, the PTEN inhibitor is administered about 1 hour to about 5 days prior to administration of the chemotherapeutic agent. In some aspects, the PTEN inhibitor is administered about 1 hour to about 4 days prior to administration of the chemotherapeutic agent. In some aspects, the PTEN inhibitor is administered about 1 hour to about 3 days prior to administration of the chemotherapeutic agent. In some aspects, the PTEN inhibitor is administered about 1 hour to about 2 days prior to administration of the chemotherapeutic agent. In some aspects, the PTEN inhibitor is administered about 1 hour to about 1 day prior to administration of the chemotherapeutic agent. In some aspects, the PTEN inhibitor is administered about 1 hour to about 12 hours prior to administration of the chemotherapeutic agent. In some aspects, the PTEN inhibitor is administered about 1 hour to about 6 hours prior to administration of the chemotherapeutic agent. In some aspects, the PTEN inhibitor is administered about 1 hour to about 4 hours prior to administration of the chemotherapeutic agent. In some aspects, the PTEN inhibitor is administered about 1 hour to about 2 hours prior to administration of the chemotherapeutic agent. In some aspects, the PTEN inhibitor is administered about 5 minutes to about 1 hour prior to administration of the chemotherapeutic agent. In some aspects, the PTEN inhibitor is administered about 5 minutes to about 30 minutes prior to administration of the chemotherapeutic agent.

In some aspects, the PTEN inhibitor is administered about 2 weeks prior to administration of the chemotherapeutic agent. In some aspects, the PTEN inhibitor is administered about 13 days prior to administration of the chemotherapeutic agent. In some aspects, the PTEN inhibitor is administered about 12 days prior to administration of the chemotherapeutic agent. In some aspects, the PTEN inhibitor is administered about 11 days prior to administration of the chemotherapeutic agent. In some aspects, the PTEN inhibitor is administered about 10 days prior to administration of the chemotherapeutic agent. In some aspects, the PTEN inhibitor is administered about 9 days prior to administration of the chemotherapeutic agent. In some aspects, the PTEN inhibitor is administered about 8 days prior to administration of the chemotherapeutic agent. In some aspects, the PTEN inhibitor is administered about 1 week prior to administration of the chemotherapeutic agent. In some aspects, the PTEN inhibitor is administered about 6 days prior to administration of the chemotherapeutic agent. In some aspects, the PTEN inhibitor is administered about 5 days prior to administration of the chemotherapeutic agent. In some aspects, the PTEN inhibitor is administered about 4 days prior to administration of the chemotherapeutic agent. In some aspects, the PTEN inhibitor is administered about 3 days prior to administration of the chemotherapeutic agent. In some aspects, the PTEN inhibitor is administered about 2 days prior to administration of the chemotherapeutic agent. In some aspects, the PTEN inhibitor is administered about 1 day prior to administration of the chemotherapeutic agent. In some aspects, the PTEN inhibitor is administered about 23 hours prior to administration of the chemotherapeutic agent. In some aspects, the PTEN inhibitor is administered about 22 hours prior to administration of the chemotherapeutic agent. In some aspects, the PTEN inhibitor is administered about 21 hours prior to administration of the chemotherapeutic agent. In some aspects, the PTEN inhibitor is administered about 20 hours prior to administration of the chemotherapeutic agent. In some aspects, the PTEN inhibitor is administered about 19 hours prior to administration of the chemotherapeutic agent. In some aspects, the PTEN inhibitor is administered about 18 hours prior to administration of the chemotherapeutic agent. In some aspects, the PTEN inhibitor is administered about 17 hours prior to administration of the chemotherapeutic agent. In some aspects, the PTEN inhibitor is administered about 16 hours prior to administration of the chemotherapeutic agent. In some aspects, the PTEN inhibitor is administered about 15 hours prior to administration of the chemotherapeutic agent. In some aspects, the PTEN inhibitor is administered about 14 hours prior to administration of the chemotherapeutic agent. In some aspects, the PTEN inhibitor is administered about 13 hours prior to administration of the chemotherapeutic agent. In some aspects, the PTEN inhibitor is administered about 12 hours prior to administration of the chemotherapeutic agent. In some aspects, the PTEN inhibitor is administered about 11 hours prior to administration of the chemotherapeutic agent. In some aspects, the PTEN inhibitor is administered about 10 hours prior to administration of the chemotherapeutic agent. In some aspects, the PTEN inhibitor is administered about 9 hours prior to administration of the chemotherapeutic agent. In some aspects, the PTEN inhibitor is administered about 8 hours prior to administration of the chemotherapeutic agent. In some aspects, the PTEN inhibitor is administered about 7 hours prior to administration of the chemotherapeutic agent. In some aspects, the PTEN inhibitor is administered about 6 hours prior to administration of the chemotherapeutic agent. In some aspects, the PTEN inhibitor is administered about 5 hours prior to administration of the chemotherapeutic agent. In some aspects, the PTEN inhibitor is administered about 4 hours prior to administration of the chemotherapeutic agent. In some aspects, the PTEN inhibitor is administered about 3 hours prior to administration of the chemotherapeutic agent. In some aspects, the PTEN inhibitor is administered about 2 hours prior to administration of the chemotherapeutic agent. In some aspects, the PTEN inhibitor is administered about 1 hour prior to administration of the chemotherapeutic agent. In some aspects, the PTEN inhibitor is administered about 50 minutes prior to administration of the chemotherapeutic agent. In some aspects, the PTEN inhibitor is administered about 40 minutes prior to administration of the chemotherapeutic agent. In some aspects, the PTEN inhibitor is administered about 30 minutes prior to administration of the chemotherapeutic agent. In some aspects, the PTEN inhibitor is administered about 20 minutes prior to administration of the chemotherapeutic agent. In some aspects, the PTEN inhibitor is administered about 10 minutes prior to administration of the chemotherapeutic agent. In some aspects, the PTEN inhibitor is administered about 5 minutes prior to administration of the chemotherapeutic agent.

In some aspects, the PTEN inhibitor is coadministered with the chemotherapeutic agent. In some aspects, the PTEN inhibitor and the chemotherapeutic are administered as separate dosage forms. In some aspects, the PTEN inhibitor and the chemotherapeutic are not administered at the same time. In some aspects, the PTEN inhibitor is administered within an hour of administration of the chemotherapeutic agent. In some aspects, the PTEN inhibitor is administered within 2 hours of administration of the chemotherapeutic agent. In some aspects, the PTEN inhibitor is administered within 3 hours of administration of the chemotherapeutic agent. In some aspects, the PTEN inhibitor is administered within 4 hours of administration of the chemotherapeutic agent. In some aspects, the PTEN inhibitor is administered within 5 hours of administration of the chemotherapeutic agent. In some aspects, the PTEN inhibitor is administered within 6 hours of administration of the chemotherapeutic agent. In some aspects, the PTEN inhibitor is administered within 7 hours of administration of the chemotherapeutic agent. In some aspects, the PTEN inhibitor is administered within 8 hours of administration of the chemotherapeutic agent. In some aspects, the PTEN inhibitor is administered within 9 hours of administration of the chemotherapeutic agent. In some aspects, the PTEN inhibitor is administered within 10 hours of administration of the chemotherapeutic agent. In some aspects, the PTEN inhibitor is administered within 11 hours of administration of the chemotherapeutic agent. In some aspects, the PTEN inhibitor is administered within 12 hours of administration of the chemotherapeutic agent. The PTEN inhibitor can be administered either before or after the chemotherapeutic agent if they are coadministered.

In some aspects, the PTEN inhibitor is administered after administration of the chemotherapeutic agent. In some aspects, the PTEN inhibitor is administered about 1 hour to about 2 weeks after administration of the chemotherapeutic agent. In some aspects, the PTEN inhibitor is administered about 1 hour to about 1 week after administration of the chemotherapeutic agent. In some aspects, the PTEN inhibitor is administered about 1 hour to about 6 days after administration of the chemotherapeutic agent. In some aspects, the PTEN inhibitor is administered about 1 hour to about 5 days after administration of the chemotherapeutic agent. In some aspects, the PTEN inhibitor is administered about 1 hour to about 4 days after administration of the chemotherapeutic agent. In some aspects, the PTEN inhibitor is administered about 1 hour to about 3 days after administration of the chemotherapeutic agent. In some aspects, the PTEN inhibitor is administered about 1 hour to about 2 days after administration of the chemotherapeutic agent. In some aspects, the PTEN inhibitor is administered about 1 hour to about 1 day after administration of the chemotherapeutic agent. In some aspects, the PTEN inhibitor is administered about 1 hour to about 12 hours after administration of the chemotherapeutic agent. In some aspects, the PTEN inhibitor is administered about 1 hour to about 6 hours after administration of the chemotherapeutic agent. In some aspects, the PTEN inhibitor is administered about 1 hour to about 4 hours after administration of the chemotherapeutic agent. In some aspects, the PTEN inhibitor is administered about 1 hour to about 2 hours after administration of the chemotherapeutic agent. In some aspects, the PTEN inhibitor is administered about 5 minutes to about 1 hour after administration of the chemotherapeutic agent. In some aspects, the PTEN inhibitor is administered about 5 minutes to about 30 minutes after administration of the chemotherapeutic agent.

In some aspects, the PTEN inhibitor is administered about 2 weeks after administration of the chemotherapeutic agent. In some aspects, the PTEN inhibitor is administered about 13 days after administration of the chemotherapeutic agent. In some aspects, the PTEN inhibitor is administered about 12 days after administration of the chemotherapeutic agent. In some aspects, the PTEN inhibitor is administered about 11 days after administration of the chemotherapeutic agent. In some aspects, the PTEN inhibitor is administered about 10 days after administration of the chemotherapeutic agent. In some aspects, the PTEN inhibitor is administered about 9 days after administration of the chemotherapeutic agent. In some aspects, the PTEN inhibitor is administered about 8 days after administration of the chemotherapeutic agent. In some aspects, the PTEN inhibitor is administered about 1 week after administration of the chemotherapeutic agent. In some aspects, the PTEN inhibitor is administered about 6 days after administration of the chemotherapeutic agent. In some aspects, the PTEN inhibitor is administered about 5 days after administration of the chemotherapeutic agent. In some aspects, the PTEN inhibitor is administered about 4 days after administration of the chemotherapeutic agent. In some aspects, the PTEN inhibitor is administered about 3 days after administration of the chemotherapeutic agent. In some aspects, the PTEN inhibitor is administered about 2 days after administration of the chemotherapeutic agent. In some aspects, the PTEN inhibitor is administered about 1 day after administration of the chemotherapeutic agent. In some aspects, the PTEN inhibitor is administered about 23 hours after administration of the chemotherapeutic agent. In some aspects, the PTEN inhibitor is administered about 22 hours after administration of the chemotherapeutic agent. In some aspects, the PTEN inhibitor is administered about 21 hours after administration of the chemotherapeutic agent. In some aspects, the PTEN inhibitor is administered about 20 hours after administration of the chemotherapeutic agent. In some aspects, the PTEN inhibitor is administered about 19 hours after administration of the chemotherapeutic agent. In some aspects, the PTEN inhibitor is administered about 18 hours after administration of the chemotherapeutic agent. In some aspects, the PTEN inhibitor is administered about 17 hours after administration of the chemotherapeutic agent. In some aspects, the PTEN inhibitor is administered about 16 hours after administration of the chemotherapeutic agent. In some aspects, the PTEN inhibitor is administered about 15 hours after administration of the chemotherapeutic agent. In some aspects, the PTEN inhibitor is administered about 14 hours after administration of the chemotherapeutic agent. In some aspects, the PTEN inhibitor is administered about 13 hours after administration of the chemotherapeutic agent. In some aspects, the PTEN inhibitor is administered about 12 hours after administration of the chemotherapeutic agent. In some aspects, the PTEN inhibitor is administered about 11 hours after administration of the chemotherapeutic agent. In some aspects, the PTEN inhibitor is administered about 10 hours after administration of the chemotherapeutic agent. In some aspects, the PTEN inhibitor is administered about 9 hours after administration of the chemotherapeutic agent. In some aspects, the PTEN inhibitor is administered about 8 hours after administration of the chemotherapeutic agent. In some aspects, the PTEN inhibitor is administered about 7 hours after administration of the chemotherapeutic agent. In some aspects, the PTEN inhibitor is administered about 6 hours after administration of the chemotherapeutic agent. In some aspects, the PTEN inhibitor is administered about 5 hours after administration of the chemotherapeutic agent. In some aspects, the PTEN inhibitor is administered about 4 hours after administration of the chemotherapeutic agent. In some aspects, the PTEN inhibitor is administered about 3 hours after administration of the chemotherapeutic agent. In some aspects, the PTEN inhibitor is administered about 2 hours after administration of the chemotherapeutic agent. In some aspects, the PTEN inhibitor is administered about 1 hour after administration of the chemotherapeutic agent. In some aspects, the PTEN inhibitor is administered about 50 minutes after administration of the chemotherapeutic agent. In some aspects, the PTEN inhibitor is administered about 40 minutes after administration of the chemotherapeutic agent. In some aspects, the PTEN inhibitor is administered about 30 minutes after administration of the chemotherapeutic agent. In some aspects, the PTEN inhibitor is administered about 20 minutes after administration of the chemotherapeutic agent. In some aspects, the PTEN inhibitor is administered about 10 minutes after administration of the chemotherapeutic agent. In some aspects, the PTEN inhibitor is administered about 5 minutes after administration of the chemotherapeutic agent.

In some aspects, the PTEN inhibitor can be administered during a dosing regimen of a chemotherapeutic agent. In some aspects, the PTEN inhibitor can be administered during a 28-day dosing regimen of a chemotherapeutic agent. In some aspects, the PTEN inhibitor can be administered after completion of a dosing regimen of a chemotherapeutic agent. In some aspects, the PTEN inhibitor can be administered after completion of a 28-day dosing regimen of a chemotherapeutic agent.

In some aspects, the PTEN inhibitor is administered in an amount effective to increase the tolerated duration of treatment with the chemotherapeutic agent or the tolerated amount of treatment with the chemotherapeutic agent.

In some aspects, the chemotherapeutic agent is administered as a treatment for a hematological cancer (e.g., multiple myeloma, leukemias, lymphoma, etc) or solid tumor cancer (e.g., skin cancer such as melanoma, head and neck cancer, such as esophageal cancer, bladder cancer, lung cancer, such as non-small cell lung cancer, adenocarcinoma of the lung, central nervous system cancer such as lung metastases in the brain or neuroblastoma, pancreatic cancer, breast cancer, mesothelioma, cervical cancer or intestinal cancer such as colon or rectum adenocarcinoma). In some aspects, the chemotherapeutic agent is administered as a treatment for a cancer is selected from the group consisting of: skin cancer, malignant peripheral nerve sheath cancer, leukemia, lymphoma, histiocytic neoplasm, lung cancer, breast cancer, ovarian cancer, renal cancer, colorectal cancer, thyroid cancer, cholangiocarcinoma, urothelial cancer, uterine neoplasm, gastric cancer, sarcoma, bladder cancer, head and neck cancer, endometrial cancer, esophageal cancer, adenoid cystic carcinoma, gallbladder cancer, prostate cancer, oral cancer, cervical cancer, pancreatic cancer, melanoma, hepatocellular cancer, biliary tract cancer, and serous carcinoma of the peritoneum.

In some aspects, the present disclosure provides a method of treating exposure to nuclear radiation in a subject in need thereof, the method comprising administering to the subject an effective amount of a PTEN inhibitor selected from the group consisting of: verteporfin or a pharmaceutically acceptable salt thereof; candicidin or a pharmaceutically acceptable salt thereof; cyanocobalamin or a pharmaceutically acceptable salt thereof; 1-palmitoyl-2-oleoyl-sn-glycero-3-(phospho-rac-(1-glycerol)) or a pharmaceutically acceptable salt thereof; fondaparinux or a pharmaceutically acceptable salt thereof; trypan blue free acid or a pharmaceutically acceptable salt thereof; indocyanine green acid form or a pharmaceutically acceptable salt thereof; DL-dimyristoylphosphatidylglycerol or a pharmaceutically acceptable salt thereof; and tannic acid or a pharmaceutically acceptable salt thereof.

In some aspects, the PTEN inhibitor is administered in an amount effective to reduce apoptosis in the subject caused by exposure to nuclear radiation. In some aspects, the PTEN inhibitor is administered in an amount effective to reduce bone marrow loss in the subject caused by exposure to nuclear radiation. In some aspects, the PTEN inhibitor is administered in an amount effective to reduce damage to the gastrointestinal epithelium in the subject caused by exposure to nuclear radiation. In some aspects, the PTEN inhibitor is administered in an amount effective to reduce an increased risk of infection in the subject caused by exposure to nuclear radiation.

In some aspects, the PTEN inhibitor is administered about 1 hour to about 2 weeks after exposure to nuclear radiation. In some aspects, the PTEN inhibitor is administered about 1 hour to about 1 week after exposure to nuclear radiation. In some aspects, the PTEN inhibitor is administered about 1 hour to about 6 days after exposure to nuclear radiation. In some aspects, the PTEN inhibitor is administered about 1 hour to about 5 days after exposure to nuclear radiation. In some aspects, the PTEN inhibitor is administered about 1 hour to about 4 days after exposure to nuclear radiation. In some aspects, the PTEN inhibitor is administered about 1 hour to about 3 days after exposure to nuclear radiation. In some aspects, the PTEN inhibitor is administered about 1 hour to about 2 days after exposure to nuclear radiation. In some aspects, the PTEN inhibitor is administered about 1 hour to about 1 day after exposure to nuclear radiation. In some aspects, the PTEN inhibitor is administered about 1 hour to about 12 hours after exposure to nuclear radiation. In some aspects, the PTEN inhibitor is administered about 1 hour to about 6 hours after exposure to nuclear radiation. In some aspects, the PTEN inhibitor is administered about 1 hour to about 4 hours after exposure to nuclear radiation. In some aspects, the PTEN inhibitor is administered about 1 hour to about 2 hours after exposure to nuclear radiation. In some aspects, the PTEN inhibitor is administered about 5 minutes to about 1 hour after exposure to nuclear radiation. In some aspects, the PTEN inhibitor is administered about 5 minutes to about 30 minutes after exposure to nuclear radiation.

In some aspects, the PTEN inhibitor is administered about 2 weeks after exposure to nuclear radiation. In some aspects, the PTEN inhibitor is administered about 13 days after exposure to nuclear radiation. In some aspects, the PTEN inhibitor is administered about 12 days after exposure to nuclear radiation. In some aspects, the PTEN inhibitor is administered about 11 days after exposure to nuclear radiation. In some aspects, the PTEN inhibitor is administered about 10 days after exposure to nuclear radiation. In some aspects, the PTEN inhibitor is administered about 9 days after exposure to nuclear radiation. In some aspects, the PTEN inhibitor is administered about 8 days after exposure to nuclear radiation. In some aspects, the PTEN inhibitor is administered about 1 week after exposure to nuclear radiation. In some aspects, the PTEN inhibitor is administered about 6 days after exposure to nuclear radiation. In some aspects, the PTEN inhibitor is administered about 5 days after exposure to nuclear radiation. In some aspects, the PTEN inhibitor is administered about 4 days after exposure to nuclear radiation. In some aspects, the PTEN inhibitor is administered about 3 days after exposure to nuclear radiation. In some aspects, the PTEN inhibitor is administered about 2 days after exposure to nuclear radiation. In some aspects, the PTEN inhibitor is administered about 1 day after exposure to nuclear radiation. In some aspects, the PTEN inhibitor is administered about 23 hours after exposure to nuclear radiation. In some aspects, the PTEN inhibitor is administered about 22 hours after exposure to nuclear radiation. In some aspects, the PTEN inhibitor is administered about 21 hours after exposure to nuclear radiation. In some aspects, the PTEN inhibitor is administered about 20 hours after exposure to nuclear radiation. In some aspects, the PTEN inhibitor is administered about 19 hours after exposure to nuclear radiation. In some aspects, the PTEN inhibitor is administered about 18 hours after exposure to nuclear radiation. In some aspects, the PTEN inhibitor is administered about 17 hours after exposure to nuclear radiation. In some aspects, the PTEN inhibitor is administered about 16 hours after exposure to nuclear radiation. In some aspects, the PTEN inhibitor is administered about 15 hours after exposure to nuclear radiation. In some aspects, the PTEN inhibitor is administered about 14 hours after exposure to nuclear radiation. In some aspects, the PTEN inhibitor is administered about 13 hours after exposure to nuclear radiation. In some aspects, the PTEN inhibitor is administered about 12 hours after exposure to nuclear radiation. In some aspects, the PTEN inhibitor is administered about 11 hours after exposure to nuclear radiation. In some aspects, the PTEN inhibitor is administered about 10 hours after exposure to nuclear radiation. In some aspects, the PTEN inhibitor is administered about 9 hours after exposure to nuclear radiation. In some aspects, the PTEN inhibitor is administered about 8 hours after exposure to nuclear radiation. In some aspects, the PTEN inhibitor is administered about 7 hours after exposure to nuclear radiation. In some aspects, the PTEN inhibitor is administered about 6 hours after exposure to nuclear radiation. In some aspects, the PTEN inhibitor is administered about 5 hours after exposure to nuclear radiation. In some aspects, the PTEN inhibitor is administered about 4 hours after exposure to nuclear radiation. In some aspects, the PTEN inhibitor is administered about 3 hours after exposure to nuclear radiation. In some aspects, the PTEN inhibitor is administered about 2 hours after exposure to nuclear radiation. In some aspects, the PTEN inhibitor is administered about 1 hour after exposure to nuclear radiation. In some aspects, the PTEN inhibitor is administered about 50 minutes after exposure to nuclear radiation. In some aspects, the PTEN inhibitor is administered about 40 minutes after exposure to nuclear radiation. In some aspects, the PTEN inhibitor is administered about 30 minutes after exposure to nuclear radiation. In some aspects, the PTEN inhibitor is administered about 20 minutes after exposure to nuclear radiation. In some aspects, the PTEN inhibitor is administered about 10 minutes after exposure to nuclear radiation. In some aspects, the PTEN inhibitor is administered about 5 minutes after exposure to nuclear radiation.

In some aspects, the subject has been diagnosed with Acute Radiation Syndrome.

In some aspects, the present disclosure provides a method of preventing Acute Radiation Syndrome in a subject in need thereof, the method comprising administering to the subject an effective amount of a PTEN inhibitor. In some aspects, the present disclosure provides a method of preventing Acute Radiation Syndrome in a subject in need thereof, the method comprising administering to the subject an effective amount of a PTEN inhibitor selected from the group consisting of: 1-palmitoyl-2-oleoyl-sn-glycero-3-(phospho-rac-(1-glycerol)), candicidin, cobicistat, cyanocobalamin, diacetyl benzoyl lathyrol, DL-dimyristoylphosphatidylglycerol, everolimus, fondaparinux, indocyanine green acid form, levosimendan, oftasceine, tannic acid, trypan blue free acid, and verteporfin. In some aspects, the present disclosure provides a method of preventing Acute Radiation Syndrome in a subject in need thereof, the method comprising administering to the subject an effective amount of a PTEN inhibitor selected from the group consisting of: verteporfin or a pharmaceutically acceptable salt thereof; candicidin or a pharmaceutically acceptable salt thereof; cyanocobalamin or a pharmaceutically acceptable salt thereof; 1-palmitoyl-2-oleoyl-sn-glycero-3-(phospho-rac-(1-glycerol)) or a pharmaceutically acceptable salt thereof; fondaparinux or a pharmaceutically acceptable salt thereof; trypan blue free acid or a pharmaceutically acceptable salt thereof; indocyanine green acid form or a pharmaceutically acceptable salt thereof; DL-dimyristoylphosphatidylglycerol or a pharmaceutically acceptable salt thereof; and tannic acid or a pharmaceutically acceptable salt thereof; wherein the PTEN inhibitor is administered prior to or during exposure of the subject to nuclear radiation.

In some aspects, the PTEN inhibitor is administered prior to exposure to nuclear radiation. In some aspects, the PTEN inhibitor is administered about 1 hour to about 2 weeks prior to exposure to nuclear radiation. In some aspects, the PTEN inhibitor is administered about 1 hour to about 1 week prior to exposure to nuclear radiation. In some aspects, the PTEN inhibitor is administered about 1 hour to about 6 days prior to exposure to nuclear radiation. In some aspects, the PTEN inhibitor is administered about 1 hour to about 5 days prior to exposure to nuclear radiation. In some aspects, the PTEN inhibitor is administered about 1 hour to about 4 days prior to exposure to nuclear radiation. In some aspects, the PTEN inhibitor is administered about 1 hour to about 3 days prior to exposure to nuclear radiation. In some aspects, the PTEN inhibitor is administered about 1 hour to about 2 days prior to exposure to nuclear radiation. In some aspects, the PTEN inhibitor is administered about 1 hour to about 1 day prior to exposure to nuclear radiation. In some aspects, the PTEN inhibitor is administered about 1 hour to about 12 hours prior to exposure to nuclear radiation. In some aspects, the PTEN inhibitor is administered about 1 hour to about 6 hours prior to exposure to nuclear radiation. In some aspects, the PTEN inhibitor is administered about 1 hour to about 4 hours prior to exposure to nuclear radiation. In some aspects, the PTEN inhibitor is administered about 1 hour to about 2 hours prior to exposure to nuclear radiation. In some aspects, the PTEN inhibitor is administered about 5 minutes to about 1 hour prior to exposure to nuclear radiation. In some aspects, the PTEN inhibitor is administered about 5 minutes to about 30 minutes prior to exposure to nuclear radiation.

In some aspects, the PTEN inhibitor is administered about 2 weeks prior to exposure to nuclear radiation. In some aspects, the PTEN inhibitor is administered about 13 days prior to exposure to nuclear radiation. In some aspects, the PTEN inhibitor is administered about 12 days prior to exposure to nuclear radiation. In some aspects, the PTEN inhibitor is administered about 11 days prior to exposure to nuclear radiation. In some aspects, the PTEN inhibitor is administered about 10 days prior to exposure to nuclear radiation. In some aspects, the PTEN inhibitor is administered about 9 days prior to exposure to nuclear radiation. In some aspects, the PTEN inhibitor is administered about 8 days prior to exposure to nuclear radiation. In some aspects, the PTEN inhibitor is administered about 1 week prior to exposure to nuclear radiation. In some aspects, the PTEN inhibitor is administered about 6 days prior to exposure to nuclear radiation. In some aspects, the PTEN inhibitor is administered about 5 days prior to exposure to nuclear radiation. In some aspects, the PTEN inhibitor is administered about 4 days prior to exposure to nuclear radiation. In some aspects, the PTEN inhibitor is administered about 3 days prior to exposure to nuclear radiation. In some aspects, the PTEN inhibitor is administered about 2 days prior to exposure to nuclear radiation. In some aspects, the PTEN inhibitor is administered about 1 day prior to exposure to nuclear radiation. In some aspects, the PTEN inhibitor is administered about 23 hours prior to exposure to nuclear radiation. In some aspects, the PTEN inhibitor is administered about 22 hours prior to exposure to nuclear radiation. In some aspects, the PTEN inhibitor is administered about 21 hours prior to exposure to nuclear radiation. In some aspects, the PTEN inhibitor is administered about 20 hours prior to exposure to nuclear radiation. In some aspects, the PTEN inhibitor is administered about 19 hours prior to exposure to nuclear radiation. In some aspects, the PTEN inhibitor is administered about 18 hours prior to exposure to nuclear radiation. In some aspects, the PTEN inhibitor is administered about 17 hours prior to exposure to nuclear radiation. In some aspects, the PTEN inhibitor is administered about 16 hours prior to exposure to nuclear radiation. In some aspects, the PTEN inhibitor is administered about 15 hours prior to exposure to nuclear radiation. In some aspects, the PTEN inhibitor is administered about 14 hours prior to exposure to nuclear radiation. In some aspects, the PTEN inhibitor is administered about 13 hours prior to exposure to nuclear radiation. In some aspects, the PTEN inhibitor is administered about 12 hours prior to exposure to nuclear radiation. In some aspects, the PTEN inhibitor is administered about 11 hours prior to exposure to nuclear radiation. In some aspects, the PTEN inhibitor is administered about 10 hours prior to exposure to nuclear radiation. In some aspects, the PTEN inhibitor is administered about 9 hours prior to exposure to nuclear radiation. In some aspects, the PTEN inhibitor is administered about 8 hours prior to exposure to nuclear radiation. In some aspects, the PTEN inhibitor is administered about 7 hours prior to exposure to nuclear radiation. In some aspects, the PTEN inhibitor is administered about 6 hours prior to exposure to nuclear radiation. In some aspects, the PTEN inhibitor is administered about 5 hours prior to exposure to nuclear radiation. In some aspects, the PTEN inhibitor is administered about 4 hours prior to exposure to nuclear radiation. In some aspects, the PTEN inhibitor is administered about 3 hours prior to exposure to nuclear radiation. In some aspects, the PTEN inhibitor is administered about 2 hours prior to exposure to nuclear radiation. In some aspects, the PTEN inhibitor is administered about 1 hour prior to exposure to nuclear radiation. In some aspects, the PTEN inhibitor is administered about 50 minutes prior to exposure to nuclear radiation. In some aspects, the PTEN inhibitor is administered about 40 minutes prior to exposure to nuclear radiation. In some aspects, the PTEN inhibitor is administered about 30 minutes prior to exposure to nuclear radiation. In some aspects, the PTEN inhibitor is administered about 20 minutes prior to exposure to nuclear radiation. In some aspects, the PTEN inhibitor is administered about 10 minutes prior to exposure to nuclear radiation. In some aspects, the PTEN inhibitor is administered about 5 minutes prior to exposure to nuclear radiation.

In some aspects, the PTEN inhibitor is administered during exposure to nuclear radiation.

In some aspects, the PTEN inhibitor to be administered in the methods described herein is verteporfin or a pharmaceutically acceptable salt thereof. In some aspects, the PTEN inhibitor to be administered in the methods described herein is verteporfin. In some aspects, the PTEN inhibitor to be administered in the methods described herein is candicidin or a pharmaceutically acceptable salt thereof. In some aspects, the PTEN inhibitor to be administered in the methods described herein is candicidin. In some aspects, the PTEN inhibitor to be administered in the methods described herein is cyanocobalamin or a pharmaceutically acceptable salt thereof. In some aspects, the PTEN inhibitor to be administered in the methods described herein is cyanocobalamin. In some aspects, the PTEN inhibitor to be administered in the methods described herein is 1-palmitoyl-2-oleoyl-sn-glycero-3-(phospho-rac-(1-glycerol)) or a pharmaceutically acceptable salt thereof. In some aspects, the PTEN inhibitor to be administered in the methods described herein is 1-palmitoyl-2-oleoyl-sn-glycero-3-(phospho-rac-(1-glycerol)). In some aspects, the PTEN inhibitor to be administered in the methods described herein is fondaparinux or a pharmaceutically acceptable salt thereof. In some aspects, the PTEN inhibitor to be administered in the methods described herein is fondaparinux. In some aspects, the PTEN inhibitor to be administered in the methods described herein is trypan blue free acid or a pharmaceutically acceptable salt thereof. In some aspects, the PTEN inhibitor to be administered in the methods described herein is trypan blue free acid. In some aspects, the PTEN inhibitor to be administered in the methods described herein is indocyanine green acid form or a pharmaceutically acceptable salt thereof. In some aspects, the PTEN inhibitor to be administered in the methods described herein is indocyanine green acid form. In some aspects, the PTEN inhibitor to be administered in the methods described herein is DL-dimyristoylphosphatidylglycerol or a pharmaceutically acceptable salt thereof. In some aspects, the PTEN inhibitor to be administered in the methods described herein is DL-dimyristoylphosphatidylglycerol. In some aspects, the PTEN inhibitor to be administered in the methods described herein is tannic acid or a pharmaceutically acceptable salt thereof. In some aspects, the PTEN inhibitor to be administered in the methods described herein is tannic acid.

In some aspects, a pharmaceutical composition comprises the PTEN inhibitor. In some aspects, the pharmaceutical composition further comprises a pharmaceutically acceptable carrier.

In some aspects, the pharmaceutical composition is a solid dosage form. In some aspects, the pharmaceutical composition is a tablet or capsule. In some aspects, the pharmaceutical composition is a tablet. In some aspects, the pharmaceutical composition is a capsule.

In some aspects, the pharmaceutical composition is for oral administration.

In some aspects, the pharmaceutical composition is administered parenterally. In some aspects, the pharmaceutical composition is administered intravenously. In some aspects, the pharmaceutical composition is administered intramuscularly. In some aspects, the pharmaceutical composition is administered subcutaneously.

In some aspects, the subject is a human.

In some aspects, administration of an amount of the PTEN inhibitor is as effective or more effective in activating NFκB in the subject as administration of an equimolar amount of a flagellin protein purified from *Salmonella enterica*.

EXAMPLES

Example 1: PTEN Inhibitor Screen

Candidate PTEN inhibitor compounds were identified and screened for PTEN inhibition in vitro. Human recombinant PTEN purified from *Escherichia coli* was assayed for conversion of synthetic phosphotyrosine analog 6,8-difluoro-4-methylumbelliferyl phosphate (DiFMUP) to 6,8-difluoro-7-hydroxy-4-methylcoumarin (DiFMU) in the presence of the various candidate PTEN inhibitors. The reaction was carried out at 37° C. for 1 hour in a reaction mixture containing 100 µM of DiFMUP, 50 mM Tris-HCl (pH 8.5), 0.01% bovine serum albumin, 1 mM dithiothreitol, and 2 mM ethylenediaminetetraacetic acid. PTEN activity was measured by spectrofluorometric quantitation of increasing DiFMU over time. TABLE 1 shows a selection of candidate PTEN inhibitors, the degree of PTEN inhibition observed in vitro, and the concentration of the candidate PTEN inhibitor at which 50% PTEN activity was determined ($IC_{50}$).

TABLE 1

PTEN Inhibition Screen

| Candidate PTEN Inhibitor | Concentration (µM) | % Inhibition | $IC_{50}$ (µM) |
|---|---|---|---|
| Verteporfin | 10 | 98 | 5.71 |
| tannic acid | 10 | 92 | 0.34 |
| Candicidin | 10 | 91 | 1.63 |
| Cyanocobalamin | 10 | 85 | 3.08 |
| 1-palmitoyl-2-oleoyl-sn-glycero-3-(phospho-rac-(1-glycerol)) | 10 | 85 | 1.79 |
| Fondaparinux | 10 | 80 | 2.77 |
| trypan blue free acid | 10 | 79 | 4.41 |
| indocyanine green acid form | 10 | 74 | 2.96 |
| DL-dimyristoylphosphatidylglycerol | 10 | 71 | 3.99 |
| Oftasceine | 10 | 37 | >10 |
| Everolimus | 10 | 33 | >10 |
| diacetyl benzoyl lathyrol | 10 | 25 | >10 |
| Cobicistat | 10 | 24 | >10 |
| Levosimendan | 10 | 24 | >10 |
| vinorelbine | 10 | 19 | >10 |
| afamelanotide | 10 | 16 | >10 |
| atracurium besylate | 10 | 16 | >10 |
| flavin adenine dinucleotide | 10 | 13 | >10 |
| mitotane | 10 | 13 | >10 |
| atosiban | 10 | 12 | >10 |
| netupitant | 10 | 12 | >10 |
| fidaxomicin | 10 | 11 | >10 |
| pancuronium | 10 | 11 | >10 |
| bisoctrizole | 10 | 5 | >10 |
| somatostatin | 10 | 5 | >10 |
| atorvastatin | 10 | 4 | >10 |
| natamycin | 10 | 3 | >10 |
| sirolimus | 10 | 3 | >10 |
| telaprevir | 10 | 3 | >10 |
| etonogestrel | 10 | 2 | >10 |
| hyaluronic acid | 10 | 2 | >10 |
| nitisinone | 10 | 1 | >10 |
| carbetocin | 10 | 1 | >10 |

OTHER ASPECTS

All publications, patents, and patent applications mentioned in this specification are incorporated herein by reference in their entirety to the same extent as if each individual publication, patent, or patent application was specifically and individually indicated to be incorporated by reference in its entirety. Where a term in the present application is found to be defined differently in a document incorporated herein by reference, the definition provided herein is to serve as the definition for the term.

While the invention has been described in connection with specific aspects thereof, it will be understood that invention is capable of further modifications and this application is intended to cover any variations, uses, or adaptations following, in general, the principles and including such departures from the present disclosure that come within known or customary practice within the art to which the invention pertains and can be applied to the essential features hereinbefore set forth, and follows in the scope of the claimed.

What is claimed:

1. A method of ameliorating a disease, disorder, syndrome, or condition amenable to amelioration by a PTEN inhibitor in a subject in need thereof, wherein the disease, disorder, syndrome, or condition is acute radiation syndrome, comprising administering to the subject an effective amount of a PTEN inhibitor selected from the group consisting of:
   verteporfin or a pharmaceutically acceptable salt thereof;
   candicidin or a pharmaceutically acceptable salt thereof;
   cyanocobalamin or a pharmaceutically acceptable salt thereof,
   1-palmitoyl-2-oleoyl-sn-glycero-3-(phospho-rac-(1-glycerol)) or a pharmaceutically acceptable salt thereof;
   fondaparinux or a pharmaceutically acceptable salt thereof;
   trypan blue free acid or a pharmaceutically acceptable salt thereof;
   indocyanine green acid form or a pharmaceutically acceptable salt thereof;
   DL-dimyristoylphosphatidylglycerol or a pharmaceutically acceptable salt thereof; and
   tannic acid or a pharmaceutically acceptable salt thereof.

2. The method of claim 1, comprising administering to the subject an effective amount of a PTEN inhibitor wherein amelioration of the disease, disorder, syndrome, or condition requires regenerating bone marrow.

3. The method of claim 2, wherein the subject experiences bone marrow loss as a result of exposure to nuclear radiation.

4. The method of claim 1, comprising administering to the subject an effective amount of a PTEN inhibitor wherein amelioration of the disease, disorder, syndrome, or condition requires ameliorating exposure to nuclear radiation.

5. The method of claim 4, wherein the PTEN inhibitor is administered in an amount effective to reduce apoptosis, bone marrow loss, damage to the gastrointestinal epithelium, or an increased risk of infection in the subject caused by exposure to nuclear radiation.

6. The method of claim 4, wherein the PTEN inhibitor is administered about 1 hour to about 2 weeks after exposure to nuclear radiation.

7. The method of claim 1, comprising administering to the subject an effective amount of a PTEN inhibitor wherein amelioration of the disease, disorder, syndrome, or condition reduces the likelihood of Acute Radiation Syndrome.

8. The method of claim 7, wherein the PTEN inhibitor is administered during exposure to nuclear radiation.

9. The method of claim 1, wherein a pharmaceutical composition comprises the PTEN inhibitor.

10. The method of claim 9, wherein the pharmaceutical composition is a solid dosage form, or a tablet or capsule.

11. The method of claim 9, wherein the pharmaceutical composition is for oral, parenteral, intravenous, intramuscular, or subcutaneous administration.

12. The method of claim 1, wherein the subject is a human.

13. The method of claim 1, wherein administration of an amount of the PTEN inhibitor is as effective or more effective in activating NFκB in the subject as administration of an equimolar amount of a flagellin protein purified from *Salmonella enterica*.

\* \* \* \* \*